magnesium phosphide and aluminum phosphide, (2) a thermally decomposable material, comprising a chemical compound which releases a gas in the temperature range between 20° and 65° C to give a vapor pressure of at least 50 Torr., in amount of about 10 to 30 percent by weight, and (3) about 2 to 14 percent by weight of ethylene oxide polymer having a molecular weight of between 4000 and 12000, and subsequently pressing the mixture to form pressed bodies.

12. A process as claimed in claim 11, in which at least one compound selected from the group consisting of sodium oxide, sodium hydroxide and potassium hydroxide is also mixed together with at least one phosphide selected from the group consisting of magnesium phosphide and aluminium phosphide, the thermally decomposable material, and the ethylene oxide polymer having a molecular weight of between 4000 and 12000.

13. A process as claimed in claim 12, in which each component of the mixture is present in a finely-dispersed form.

14. A process as claimed in claim 11, in which powdery ethylene oxide polymer is used having granular sizes of less than $100\mu$.

15. A process as claimed in claim 14, in which the powdery ethylene oxide polymer has granular sizes of between 5 and $75\mu$.

16. A process as claimed in claim 11, in which the thermally decomposable material is ammonium carbamate.

17. A process as claimed in claim 11, in which the pressed bodies are in form of tablets or pellets.

* * * * *

PEPTIDES HAVING AN ANTIHYPERTENSIVE EFFECT

The present invention relates to new peptide derivatives having antihypertensive activity and to a process for their manufacture.

German Offenlegungsschrift No. 2,323,322 teaches that peptides of formula

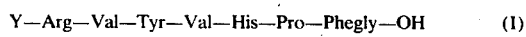

in which X is a radical of an aliphatic carboxylic acid having up to 5 carbon atoms which may carry COOH—, CONH₂—, NH₂— or carbo-benzoxy-amino (NHZ) groups or a phthalic acid radical, and Phegly—OH is the L—C—phenyl glycine residue, are antagonists of angiotensin II (AT II).

It has now been found that peptides of formula I

Y—Arg—Val—Tyr—Val—His—Pro—Phegly—OH    (I)

in which Y stands for the sarcosyl, succinamoyl or succinoyl radical, have a longer and stronger action as antagonists of angiotensin II than the above-cited known compounds.

Hence, the present invention relates to peptides of formula I with Y defined as above.

This invention further relates to a process for the manufacture of these compounds, which comprises condensing or reacting an N-protected sarcosine or succinic acid monoamide or anhydride with a peptide of formula II

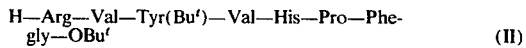

and splitting off the protective groups by a treatment with an acid.

The present invention moreover relates to pharmaceutical composition containing an effective amount of a compound of formula I, as well as to a method for preparing such a pharmaceutical composition.

As N-protective group, the tert.-butyloxy carbonyl radical (Boc) which is capable of being split off, as are the protective groups in peptide II, by treatment with an acid, for example tri-fluoroacetic acid or hydrochloric acid in dioxan or acetic acid, is preferably suitable. Further protective groups are, for example, the α,α-dimethyl-3,5-dimethoxy-benzyloxy-carbonyl (Ddz), o-nitrophenyl sulfenyl(NPS) or trityl group.

For formation of the bond between the reaction components, all of the conventional methods of peptide chemistry may be used. Dicyclo-hexyl carbodiimide (DCC), optionally in the presence of N-hydroxy succinimide or 1-hydroxy benzotriazole or analogous compounds as mentioned in Chem. Ber. 103, (1970), page 788, is preferably used. It is also possible to use activated esters of sarcosin or succinic acid, for example with 4-nitrophenol, 2,4,5-trichlorophenol, pentachlorophenol, N-hydroxy-succinimide and similar compounds. When trichloro or nitrophenyl esters are used, the aminolysis may substantially be accelerated by adding acidic N-hydroxy compounds, for example those mentioned in "Chemistry and Biology of Peptides," Ed. Meienhofer, Ann. Arbor Science Publishers, (1972), pages 343 to 350. Especially useful catalysts are, for example, 1-hydroxy-benzotriazole and 2-hydroxy pyridine. As solvents, for example dimethylformamide, dimethylacetamide, phosphoric acid tris-dimethylamide or dimethyl sulfoxide, optionally in admixture with one another, may be mentioned. The succinoyl derivative may also be prepared using the anhydride as an activated compound. For this reaction, pyridine is also suitable as a solvent.

The protective groups are cleft from the reaction products by treatment with an acid, for example trifluoroacetic acid or about 1.5N hydrochloric acid in glacial acetic acid or 3 to 6N hydrochloric acid in dioxan.

The compounds of the invention are diagnostic agents for the differential diagnosis of hypertonia and for the treatment of renin-angiotensin-induced forms of hypertonia.

Apart from being superior to the above-cited angiotensin II peptides, the compounds of the invention are also superior to angiotensin inhibitors, such as [1-sarcosine,5-valine, 8-alanine] angiotensin II, known to be highly active.

Thus, the following data relating to the potency and duration of the antagonistic activity were found:

|  | Inhibiting effect in percent | | | duration of action in min. |
|---|---|---|---|---|
|  | 0.5mcg/kg i.v. AT II | 1mcg/kg i.v. AT II | 2mcg/kg i.v. AT II | 0.1mg/kg i.v. |
| Peptide | | | | |
| [Suc¹,Val⁵pgl⁸] AT II | 98 | 94 | 92 | 89±22 |
| 10mcg/kg/min i.v. | 98 | 94 | 92 | |
| 5 " | 88 | 94 | 93 | |
| 1 " | 42 | 51 | 55 | |
| [Sar¹,Val⁵Ala⁸] AT II | | | | 66±21 |
| 10mcg/kg/min i.v. | 88 | 90 | 89 | |
| 5 " | 63 | 76 | 75 | |
| 1 " | 0 | 22 | 31 | |
| [Suc¹, Ile⁵,Pgl⁸]AT II | | | | 51±8 |
| 10mcg/kg/min i.v. | 40 | 89 | 92 | |
| 5 " | 33 | 52 | 64 | |
| 1 " | 15 | 0 | 13 | |

Suc = succinamoyl, Pgl = Phegly (= C-phenyl glycine)
Sar = Sarcosyl
Potency and duration of action of [Sar¹, Val⁵, Pgl⁸]AT II are within the range of the figures for the Suc¹- analog.

The potency of the AT II analogs is determined by measuring the increase in blood pressure caused by increasing amounts of AT II with and without infusion of the analog to be tested, at different dosages; duration of action is determined on the basis of the time during which a single injection of the analog to be tested is effective under permanent infusion of AT II.

petroleum ether. The precipitate was suction-filtered after having stood overnight at +4° C, and dried in vacuo over $P_2O_5$.

Yield: 715 g (92% of the theoretical yield), $[\alpha]_D = -16.2°$ (c = 1, $CH_3OH$).

b. Z—Val—Tyr(Bu')—OH

68 Grams of Z—Val—Tyr(Bu')—$OCH_3$ were dissolved in a mixture of 350 ml of dioxan and 150 ml of water. While controlling the pH-value electrometrically (pH>12), 140 ml of 1N sodium hydroxide solution were slowly added. After saponification was complete, the solution was neutralized by means of 1N HCl, concentrated in vacuo to a small volume and acidified to pH 3 by means of hydrochloric acid. The precipitate was suction-filtered, washed with water and dried in vacuo.

Yield: 65.7 g, m.p. 116° C, $[\alpha]_D = -5.2°$ (c = 1, $CH_3OH$).

c. Z—Val—His—$OCH_3$

With exclusion of moisture, a solution of 42 g of dicyclohexyl carbodiimide in 60 ml of dimethylformamide was added at 0° C to a solution of 50.2 g (0.2 mol) of Z—Val—OH and 27 g (0.2 mol) of 1-hydroxy benzotriazole in 200 ml of dimethyl-formamide. Stirring was continued for 90 minutes at 0° C and then for 90 minutes at room temperature, the separated dicyclo-hexyl urea was suction-filtered and the filtrate was added to a solution obtained by dissolving with cooling 60 g of H—His—$OCH_3$ . 2 HCl (80% pure, 0.2 mol) and 60.8 ml of N-ethyl morpholine in 250 ml of dimethyl sulfoxide. After standing for 24 hours at room temperature, the precipitate was suction-filtered. The filtrate was concentrated in vacuo at room temperature to an oil which was triturated three times with 500 ml each of absolute ether, and the oily residue was stirred with saturated aqueous sodium carbonate solution. The solidified product was stirred with bicarbonate solution and subsequently with water and dried in vacuo.

Yield: 50.2 g, m.p. 169° – 170° C.

After reprecipitation from dimethylformamide/ether/petroleum ether, 49 g of product were obtained of m.p. 168° – 170° C; $[\alpha]_D = +5.6°$ (c = 1, DMF).

d. Z—Val—His—OH 48.8 Grams (0.121 mol) of Z—Val—His—$OCH_3$ were suspended in 700 ml of dioxan, 0.1 ml of a 1% ethanolic thymol phthalein solution was added while stirring, and in 3 successive portions (each added upon colour change of the indicator) a total of 123 ml of 1N NaOH was added. When saponification was complete, the solution was neutralized by means of 2N HCl, concentrated in vacuo at room temperature to a small volume and acidified to pH 3.0 by means of normal HCl. The precipitated oily substance solidified in an ice bath and was suction-filtered, washed with water and triturated with a small amount of ethyl acetate.

Yield: 36.4 g, m.p. 155° C, $[\alpha]_D = +27.2°$ (c = 1, $CH_3OH$).

e. Z—Val—His—Pro—Phegly—OBu'

1.9 Milliliters (0.015 mol) of N-ethyl morpholine were added at 0° C to a solution of 5.1 g (0.015 mol) of H—Pro—Phegly—OBu' . HCl, prepared according to German Offenlegungsschrift No. 2,323,322, in 35 ml of dimethylformamide, and the mixture was combined with a solution of 5.8 g (0.015 mol) of Z—Val—His—OH and 2.1 g of 1-hydroxy benzotriazole (0.015 mol) in 50 ml of dimethylformamide. While stirring at −5° C, a solution of 3.4 g of dicyclohexyl carbodiimide in 5 ml of dimethylformamide was admixed. Stirring was continued for 1 hour at 0° C and overnight at room temperature. The separated dicyclohexyl urea was suction-filtered, and the solvent was distilled off in vacuo at room temperature. The residue was dissolved in 250 ml of ethyl acetate, the ethyl acetate solution was washed with sodium carbonate solution and water, dried over magnesium sulfate, and after clarification with charcoal, concentrated in vacuo at room temperature to a small volume, and the product was finally precipitated with dry diethyl ether.

Yield: 8.5 g, m.p. 124° C; $[\alpha]_D = -17.0°$ (c = 1, $CH_3OH$).

f. H—Val—His—Pro—Phegly—OBu' . 2 HCl 8.3 Grams of Z—Val—His—Pro—Phegly—OBu' were dissolved in 200 ml of $CH_3OH$, 3 g of a 10% $Pd/BaSO_4$ catalyst were added, and the mixture was hydrogenated while stirring, with the exclusion of air, by passing hydrogen through it. The pH-value was maintained at 3.0 by adding dropwise 1N methanolic HCl. After suction-filtration of the catalyst, concentration of the solution in vacuo and precipitation of the product with dry diethyl ether, 7.1 g of a product were obtained; m.p. 170° C (with decomposition), $[\alpha]_D = -17.8°$ (c = 1, $CH_3OH$).

g. Z—Tyr(Bu')—Val—His—Pro—Phegly—OBu'

18.63 Grams (0.05 mol) of Z—Tyr(Bu')—OH and a solution of 11.3 g (0.05 mol) of dicyclohexyl carbodiimide in 16 ml of dimethyl-formamide were added successively at 0° C to a solution prepared at 0° C from 30.6 g (0.05 mol) of H—Val—His—Pro—Phegly—OBu' . 2 HCl and 12.6 ml (0.1 mol) of N-ethyl morpholine in 100 ml of dimethylformamide. Stirring was then continued for 1 hour at 0° C and for 16 hours at room temperature. The separated dicyclohexyl urea was suction-filtered, the solvent was distilled off, and the product was dissolved in ethyl acetate. The solution was washed with saturated aqueous sodium bicarbonate solution and water, dried over sodium sulfate, clarified with charcoal and concentrated in vacuo at room temperature. 44.1 Grams of a nearly colorless, amorphous solid were obtained, m.p. 109° C (decomposition), $[\alpha]_D = -15.5°$ (c = 1, $CH_3OH$).

h. H—Tyr(Bu')—Val—His—Pro—Phegly—OBu' . 2 HCl

44 Grams of Z—Tyr(Bu')—Val—His—Pro—Phegly—OBu' were dissolved in 850 ml of $CH_3OH$, and the solution was hydrogenated as in (f). After distillation of the solvent, the product was obtained as a colorless, amorphous solid.

Yield: 38.4 g, m.p. 114° C, $[\alpha]_D = +4.8°$ (c = 1, $CH_3OH$).

i. Z—Val—Tyr(Bu')—Val—His—Pro—Phegly—OBu'

38 Grams (0.04 mol) of H—Tyr(Bu')—Val—His—Pro—Phegly—OBu' and 10.12 ml (0.09 mol) of N-ethyl morpholine were dissolved at 0° C in 280 ml of dimethylformamide, then a solution of 10.1 g (0.04 mol) of Z—Val—OH and 5.4 g (0.04 mol) of 1-hydroxy benzotriazole in 80 ml of dimethylformamide was admixed. After cooling to −5° C, 9.1 g of dicyclohexyl carbodiimide dissolved in 15 ml of dimethylformamide were added. Stirring was continued for 1 hour at 0° C and for 16 hours at room temperature. After the precipitated dicyclohexyl urea had been separated, and the solvent had been distilled off in vacuo at room temperature, the residue was dissolved in ethyl acetate, the solution was washed with a 2N sodium carbonate solution, dried with sodium sulfate, clarified with charcoal, and the product was isolated by distilling off the solvent and trituration with absolute diethyl ether.

Yield: 31.7 g, m.p. 155° C (decomposition), $[\alpha]_D = -14.8°$ (c = 1, DMF).

k. H—Val—Tyr(Bu$^t$)—Val—His—Pro—Phegly—OBu$^t$ . 2 HCl

A solution of 31.5 g of Z—Val—Tyr(Bu$^t$)—Val—His—Pro—Phegly—OBu$^t$ in 600 ml of methanol was hydrogenated as sub (f) and worked up.

Yield: 28.6 g, m.p. 183° C, $[\alpha]_D = +9.6°$ (c = 1, DMF).

l. Z$_3$Arg—Val—Tyr—Val—His—Pro—Phegly—OBu$^t$ 6.6 Milliliters (0.052 mol) of N-ethyl morpholine were added at 0° C to a solution of 27.4 g (0.028 mol) of H—Val—Tyr(Bu$^t$)—Val—His—Pro—Phegly—OBu$^t$ in 200 ml of dimethylformamide. After addition of a solution of 16.5 g of Z$_3$Arg—OH and 3.4 g of 1-hydroxy benzotriazole in 100 ml of dimethylformamide, the mixture was cooled to −5° C. A solution of 5.9 g of dicyclohexyl carbodiimide in 15 ml of dimethylformamide was admixed while stirring. Stirring was continued for 1 hour at 0° C and for 12 hours at room temperature. The separated dicyclohexyl urea was filtered off, and the solvent was removed by distillation in vacuo at room temperature. The remaining oily substance solidified on trituration with 2N Na$_2$CO$_3$ solution and water.

Yield: 38.7 g, m.p. decomposition beginning at 135° C, $[\alpha]_D = -6.8°$ ( C = 1, DMF).

m. H—Arg—Val—Tyr(Bu$^t$)—Val—His—Pro—Phegly—OBu$^t$ . 3 HCl

A solution of 37.5 g of Z$_3$Arg—Val—Tyr(Bu$^t$)—Val—His—Pro—Phegly—OBu$^t$ in 1.3 l of methanol was hydrogenated and worked up as disclosed sub (f).

Yield: 28.2 g, m.p. 143° C (decomposition), $[\alpha]_D = -7.2°$ (c = 1, CH$_3$OH).

n. Succinamoyl—Arg—Val—Tyr(Bu$^t$)—Val—His—Pro—Phegly—OBu$^t$ 2.56 Grams (0.024 mol) of H—Arg—Val—Tyr(Bu$^t$)—Val—His—Pro—Phegly—OBu$^t$ . 3 HCl were dissolved in 26 ml of dimethylformamide at 0° C, and 0.91 ml (0.0075 mol) of N-ethyl morpholine was added. After addition of a concentrated solution of 324 mg of N-hydroxy benzotriazole (0.0037 mol) and 420 mg of succinic acid mono-amide in dimethylformamide, the mixture was cooled to −5° C while stirring, and a solution of 545 mg (0.0026 mol) of dicyclohexyl carbodiimide in 5 ml of dimethylformamide was added. Stirring was continued for 1 hour at 0° C and for 12 hours at room temperature. Separated dicyclohexyl urea was then suction-filtered, and the filtrate was concentrated in vacuo at room temperature to yield an oily residue which solidified upon trituration with dry diethyl ether. The product was washed with 2N Na$_2$CO$_3$ solution and water and dried in vacuo.

Yield: 3.4 g (crude), m.p. starting at 100° C, $[\alpha]_D = -7°$ (c = 1, DMF).

o. Succinamoyl—Arg—Val—Tyr—Val—His—Pro—Phegly—OH

2 Grams of succinamoyl—Arg—Val—Tyr(Bu$^t$)—Val—His—Pro—Phegly—OBu$^t$ were dissolved in 20 ml of 90% trifluoroacetic acid, and the solution was stirred for 60 minutes. The trifluoroacetic acid was distilled off in vacuo at 25° – 30° C, the residue was triturated with dry diethyl ether, dissolved in 100 ml of 90% methanol and passed through 40 ml of Amberlite IR 45-acetate form in a column having a diameter of 1 cm. The column packing was washed with 250 ml of 90% methanol, and the combined solutions were concentrated to dryness in vacuo at room temperature. The residue was triturated with dry diethyl ether and dried in vacuo.

Yield: 1.4 g. The crude product was purified by partition chromatography on Sephadex LH 20$^{(R)}$ (column size: 2.5 × 100 cm) in the solvent system n-butanol/acetic acid/water (2:1:10). 350 mg of crude product yielded 160 mg of a chromatographically pure product; m.p. 221° C (decomposition); $[\alpha]_D = -38.2°$ (c = 1, CH$_3$OH). After a 72-hour hydrolysis using 6N HCl at 110° C, amino acid analysis showed the following ratios:

Arg: 0.80, Val: 2.00, Tyr: 0.87, His: 0.91, Phegly: 1.02. Pro was not determined.

EXAMPLE 2 a. Boc—Sar—Arg—Val—Tyr(Bu$^t$)—Val—His—Pro—Phegly—OBu$^t$ 1.24 Grams (0.001 mol) of H—Arg—Val—Tyr(Bu$^t$)—Val—His—Pro—Phegly—OBu$^t$ . 3 HCl were dissolved in 10 ml of dimethylformamide and at 0° C 0.380 ml of N-ethyl morpholine was added while stirring. A solution of 0.55 g (1.5 mmols) of Boc-Sar-OTCP* in 2 ml of dimethylformamide was added, and 135 mg (1.0 mmol) of N-hydroxy benzotriazole were admixed. Stirring was continued for 1 hour at 0° C and for 20 hours at room temperature when the solution was concentrated to dryness at room temperature in vacuo. The residue was triturated with dry diethyl ether and dissolved in ethyl acetate. The solution was washed with sodium carbonate solution and water, dried over sodium sulfate, and the product was isolated as a colorless, amorphous powder by distilling off the ethyl acetate and triturating the residue with ether.

* -OTCP = 2,4,5-trichlorophenyl ester

Yield: 1,3 g, m.p. 142° C, $[\alpha]_D = -15.8°$ (c = 1, DMF).

b. H—Sar—Arg—Val—Tyr—Val—His—Pro—Phegly—OH 1.7 Grams of the aforementioned, protected sarcosine peptide were dissolved in 10 ml of 90% trifluoroacetic acid, and the solution was stirred for 50 minutes at room temperature. The solvent was then distilled off in vacuo at room temperature, and the residue was triturated with 100 ml of dry diethyl ether. 1.0 Gram of a colorless, amorphous powder was obtained, which was dissolved in 20 ml of 90% methanol and passed through 10 ml of Amberlite IR 45 (acetate form). Another 250 ml of 90% methanol were passed through the column, and the combined solutions were dried in vacuo at room temperature. The remaining residue was dissolved and precipitated several times from ethanol/ether.

Yield: 748 mg, m.p. 166° C (decomposition), $[\alpha]_D = -20.5°$ (c = 0.5, DMF/H$_2$O 1 : 1).

Partition chromatography on Sephadex LH 20 in the solvent system butanol/acetic acid/water (2 : 1 : 10) yielded the chromatographically pure end product, m.p. 225° C.

$[\alpha]_D = -25.0°$ (c = 0.5, DMF/H$_2$O, 1 : 1).

After a 24-hour hydrolysis using 6N HCl at 110° C, amino acid analysis was as follows:

Sar: 0.9, Arg: 0.85, Val: 1.99, Tyr: 0.80, His: 0.88, Phegly: 1.0. Pro was not determined.

We claim:

1. A peptide derivative of formula I

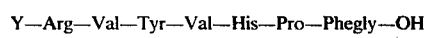

Y—Arg—Val—Tyr—Val—His—Pro—Phegly—OH    (I)

in which Y stands for the sarcosyl, succinamoyl or succinoyl radical.

2. A pharmaceutical composition suitable for the diagnosis and/or treatment of hypertonia, which comprises an effective amount of a compound as claimed in claim 1, optionally in admixture or conjunction with an inert carrier and/or preserving agent.

3. A pharmaceutical composition having prolonged duration of action in the treatment of hypertonia, which comprises an effective amount of a compound as claimed in claim 1 in the form of a complex compound with zinc and, optionally, with phosphate ions.

4. A pharmaceutical composition having prolonged duration of action in the treatment of hypertonia, which comprises an effective amount of
   a. a compound as claimed in claim 1,
   b. a gelatin derivative cross-linked with hexamethylene isocyanate, and
   c. polyphloretin phosphate.

* * * * *